(12) United States Patent
Ross et al.

(10) Patent No.: US 9,078,700 B2
(45) Date of Patent: Jul. 14, 2015

(54) FAST ADJUST EXTERNAL FIXATION CONNECTION ROD

(71) Applicant: Texas Scottish Rite Hospital for Children, Dallas, TX (US)

(72) Inventors: John David Ross, Ovilla, TX (US); Mikhail L. Samchukov, Coppell, TX (US); Alexander M. Cherkashin, Flower Mound, TX (US); John G. Birch, Dallas, TX (US)

(73) Assignee: TEXAS SCOTTISH RITE HOSPITAL FOR CHILDREN, Dallas, TX (US)

( * ) Notice: Subject to any disclaimer, the term of this patent is extended or adjusted under 35 U.S.C. 154(b) by 192 days.

(21) Appl. No.: 13/732,853

(22) Filed: Jan. 2, 2013

(65) Prior Publication Data

US 2013/0123784 A1 May 16, 2013

Related U.S. Application Data

(63) Continuation of application No. 12/865,057, filed as application No. PCT/US2009/033975 on Feb. 12, 2009, now Pat. No. 8,444,644.

(60) Provisional application No. 61/027,986, filed on Feb. 12, 2008.

(51) Int. Cl.
*A61B 17/62* (2006.01)

(52) U.S. Cl.
CPC ...................................... *A61B 17/62* (2013.01)

(58) Field of Classification Search
CPC ........................................................ A61B 17/62
USPC ............................................................. 606/56
See application file for complete search history.

(56) References Cited

U.S. PATENT DOCUMENTS 2,238,870 A 4/1941 Haynes
2,346,346 A 4/1944 Anderson
(Continued)

FOREIGN PATENT DOCUMENTS

CA 2633944 A1 7/2007
DE 3802743 A1 8/1989
(Continued)

OTHER PUBLICATIONS

Extended European Search Report, EpP 09708841.3-1654/2240085; PCT/US2009/033603, dated Dec. 2, 2013, 5 pages.
(Continued)

*Primary Examiner* — Jerry Cumberledge
*Assistant Examiner* — Nicholas Plionis
(74) *Attorney, Agent, or Firm* — Baker & McKenzie LLP

(57) ABSTRACT

The present disclosure provides various embodiments of an external fixation connection rod having articulatable joints that can be attached to external supports, such as rings. In some embodiments, the fixation connection rod includes a telescopic rod and connecting mechanisms for coupling the joints of the connection rod to the external supports. and the connecting mechanisms are operable to substantially lock the orientation of the joints. In some other embodiments, the connection rod includes a housing having parallel axial bores defined therethrough and sleeves slidably disposed in the axial bores. Also included in the present disclosure are methods of maintaining the orientation of first and second fixator rings for immobilizing bone segments.

20 Claims, 9 Drawing Sheets

(56) References Cited

U.S. PATENT DOCUMENTS

| | | |
|---|---|---|
| 4,308,863 A | 1/1982 | Fischer |
| 4,365,624 A | 12/1982 | Jaquet |
| 4,621,627 A | 11/1986 | DeBastiani et al. |
| 4,768,524 A | 9/1988 | Hardy |
| 4,889,111 A | 12/1989 | Ben-Dov |
| 4,973,331 A | 11/1990 | Pursley et al. |
| 4,988,244 A | 1/1991 | Sheldon et al. |
| 5,019,077 A | 5/1991 | De Bastiani et al. |
| 5,095,919 A | 3/1992 | Monticelli et al. |
| 5,156,605 A | 10/1992 | Pursley et al. |
| 5,180,380 A | 1/1993 | Pursley et al. |
| 5,458,599 A | 10/1995 | Adobbati |
| 5,533,418 A | 7/1996 | Wu et al. |
| 5,702,389 A | 12/1997 | Taylor et al. |
| 5,728,095 A | 3/1998 | Taylor et al. |
| 5,776,132 A | 7/1998 | Blyakher |
| 5,863,292 A | 1/1999 | Tosic |
| 5,885,283 A | 3/1999 | Gittleman |
| 5,891,143 A | 4/1999 | Taylor et al. |
| 5,928,230 A | 7/1999 | Tosic |
| 5,971,984 A | 10/1999 | Taylor et al. |
| 6,030,386 A | 2/2000 | Taylor et al. |
| 7,282,052 B2 | 10/2007 | Mullaney |
| RE40,914 E | 9/2009 | Taylor et al. |
| 8,029,505 B2 | 10/2011 | Hearn et al. |
| 8,202,273 B2 | 6/2012 | Karidis |
| 8,257,353 B2 | 9/2012 | Wong |
| 8,296,094 B2 | 10/2012 | Harrison et al. |
| 8,333,766 B2 | 12/2012 | Edelhauser et al. |
| 8,366,710 B2 | 2/2013 | Hirata et al. |
| 8,377,060 B2 | 2/2013 | Vasta et al. |
| 8,388,619 B2 | 3/2013 | Mullaney |
| 2002/0010465 A1 | 1/2002 | Koo et al. |
| 2003/0149378 A1 | 8/2003 | Peabody et al. |
| 2003/0191466 A1 | 10/2003 | Austin et al. |
| 2003/0199856 A1 | 10/2003 | Hill et al. |
| 2003/0212398 A1 | 11/2003 | Jackson |
| 2004/0073211 A1 | 4/2004 | Austin et al. |
| 2004/0097922 A1 | 5/2004 | Mullaney |
| 2004/0116926 A1 | 6/2004 | Venturini et al. |
| 2005/0192572 A1 | 9/2005 | Abdelgany et al. |
| 2005/0215997 A1 | 9/2005 | Austin et al. |
| 2005/0234457 A1 | 10/2005 | James et al. |
| 2006/0052782 A1 | 3/2006 | Morgan et al. |
| 2006/0207118 A1 | 9/2006 | Kim |
| 2006/0235389 A1 | 10/2006 | Albert et al. |
| 2007/0055234 A1 | 3/2007 | McGrath et al. |
| 2007/0055254 A1 | 3/2007 | Ihde |
| 2007/0083087 A1 | 4/2007 | Carda |
| 2007/0085496 A1 | 4/2007 | Philipp et al. |
| 2007/0225704 A1 | 9/2007 | Ziran et al. |
| 2007/0233134 A1 | 10/2007 | Bastian et al. |
| 2008/0021451 A1 | 1/2008 | Coull et al. |
| 2009/0036890 A1 | 2/2009 | Karidis |
| 2009/0036892 A1 | 2/2009 | Karidis et al. |
| 2010/0087819 A1 | 4/2010 | Mullaney |
| 2010/0262160 A1 | 10/2010 | Boyden et al. |
| 2010/0262239 A1 | 10/2010 | Boyden et al. |
| 2010/0305568 A1 | 12/2010 | Ross et al. |
| 2010/0312243 A1 | 12/2010 | Ross et al. |
| 2010/0331840 A1 | 12/2010 | Ross et al. |
| 2011/0004199 A1 | 1/2011 | Ross et al. |
| 2011/0118738 A1 | 5/2011 | Vasta et al. |
| 2011/0166572 A1 | 7/2011 | Ihde |
| 2011/0313418 A1 | 12/2011 | Nikonovas |
| 2011/0313419 A1 | 12/2011 | Mullaney |
| 2012/0041439 A1 | 2/2012 | Singh et al. |
| 2012/0130384 A1 | 5/2012 | Henderson |
| 2012/0303028 A1 | 11/2012 | Wong |
| 2012/0303029 A1 | 11/2012 | Vasta et al. |
| 2013/0018374 A1 | 1/2013 | Edelhauser et al. |

FOREIGN PATENT DOCUMENTS

| | | |
|---|---|---|
| DE | 9316164 U1 | 7/1994 |
| DE | 4421223 A1 | 12/1995 |
| DE | 102007026404 A1 | 12/2008 |
| EP | 0029298 A1 | 5/1981 |
| EP | 1239784 B1 | 4/2006 |
| EP | 1916952 B1 | 12/2009 |
| EP | 2134515 B1 | 7/2010 |
| EP | 2417923 A1 | 2/2012 |
| GB | 421788 | 12/1934 |
| GB | 2229096 A | 9/1990 |
| IT | 1259768 B | 3/1996 |
| JP | S52-003290 | 8/1978 |
| JP | S63-500499 | 2/1988 |
| JP | H02180254 A | 7/1990 |
| JP | H10290807 A | 11/1998 |
| JP | 2003508108 A | 3/2003 |
| JP | 2003508150 A | 3/2003 |
| JP | 2005-137586 | 6/2005 |
| WO | 9222268 A1 | 12/1992 |
| WO | 9626678 A1 | 9/1996 |
| WO | 9730650 A1 | 8/1997 |
| WO | 9812975 A2 | 4/1998 |
| WO | 9815231 A1 | 4/1998 |
| WO | 9920193 A1 | 4/1999 |
| WO | 9947060 A1 | 9/1999 |
| WO | 9948414 A2 | 9/1999 |
| WO | 0003647 A1 | 1/2000 |
| WO | 0115611 A1 | 3/2001 |
| WO | 0122892 A1 | 4/2001 |
| WO | 03086211 A1 | 10/2003 |
| WO | 03086212 A2 | 10/2003 |
| WO | 03086213 A2 | 10/2003 |
| WO | 2004026103 A2 | 4/2004 |
| WO | 2007002180 A2 | 1/2007 |
| WO | 2007060507 A2 | 5/2007 |
| WO | 2007139031 A1 | 12/2007 |
| WO | 2008002992 A1 | 1/2008 |
| WO | 2008134624 A1 | 11/2008 |
| WO | 2009018349 A2 | 2/2009 |
| WO | 2009018398 A2 | 2/2009 |
| WO | 2009100247 A1 | 8/2009 |
| WO | 2009100459 A1 | 8/2009 |
| WO | 2009102904 A1 | 8/2009 |
| WO | 2009105479 A1 | 8/2009 |
| WO | 2010042619 A1 | 4/2010 |
| WO | 2010104567 A1 | 9/2010 |
| WO | 2010120367 A1 | 10/2010 |
| WO | 2011017321 A2 | 2/2011 |
| WO | 2011060264 A1 | 5/2011 |
| WO | 2011060266 A1 | 5/2011 |
| WO | 2011106507 A1 | 9/2011 |
| WO | 2011146703 A1 | 11/2011 |
| WO | 2011163406 A2 | 12/2011 |

OTHER PUBLICATIONS

Japanese office action, JP Application No. 2010-546904, dated Oct. 29, 2013, 4 pages.

Japanese Office Action, dated Nov. 26, 2013, JP Application No. 2010-545284, 4 pages.

International Search Report and Written Opinion, PCT/US2013/064067, dated Jan. 31, 2014, 7 pages.

International Search Report and Written Opinion, PCT/RU2013/000203, dated Jan. 29, 2014, 23 pages.

Canero, C., et al., "Predictive (Un)distortion Model and 3-D Reconstruction by Biplane Snakes, IEEE Transactions on Medical Imaging," vol. 21, No. 9, (Sep. 2002), 14 pages.

Ghanem, R.N., et al., "Heart-Surface Reconstruction and ECG Electrodes Localization Using Fluoroscopy, Epipolar Geometry and Stereovision: Application to Noninvasive Imaging of Cardiac Electrical Activity," IEEE Transactions on Medical Imaging, vol. 22, No. 10, (Oct. 2003), 12 pages.

Li, Y., et al., "Distortion Correction and Geometric Calibration for X-Ray Angiography System," IEEE Transactions on Nuclear Science, vol. 56, No. 3, (Jun. 2009), 12 pages.

(56) References Cited

OTHER PUBLICATIONS

Selby, B.P., et al., "Patient positioning with X-ray detector self-calibration for image guided therapy," Australas Phys. Eng. Sci. Med., vol. 34, (2011), 10 pages.
Yang, J., et al., "Novel Approach for 3-D Reconstruction of Coronary Arteries From Two Uncalibrated Angiographic Images," IEEE Transactions on Image Processing, vol. 18, No. 7, (Jul. 2009), 10 pages.
Zheng, G., et al., "A 2D/3D correspondence building method for reconstruction of a patient-specific 3D bone surface model using point distribution models and calibrated X-ray images," Medical Image Analysis, vol. 13, (2009), 17 pages.
European Extended Search Report, EP Application No. 09710983.9-1654/2249721 PCT/US2009/033975, dated Apr. 4, 2014, 7 pages.
International Search Report, PCT/US2009/034413, dated Apr. 15, 2009, 1 page.
International Preliminary Report on Patentability, PCT/US2009/034413, dated Aug. 24, 2010, 7 pages.
Extended European Search Report, Application No. 09712412.7-1526, PCT/US2009/034413, dated Dec. 3, 2012, 10 pages.
International Search Report, PCT/US2010/056541, dated Jan. 12, 2011, 1 page.
International Preliminary Report on Patentability, PCT/US2010/056541, Date of issuance May 15, 2012, 7 page.
International Preliminary Report on Patentability, PCT/US2010/056539, Date of issuance May 15, 2012, 9 pages.
International Search Report, PCT/US2010/056539, Dated Jan. 18, 2011, 2 pages.
Steffen Schumann ,et al., "Calibration of X-ray radiographs and its feasible application for 2D/3D reconstruction of the proximal femur" (2008), 4 pages.
Jetzki S., et al., "Fluoroscopy-Based 3-D Reconstruction of Femoral Bone Cement: A New Approach for Revision Total Hip Replacement," (2005), 12 pages.
Guoyan Zheng, et al., "3-D reconstruction of a surface model of the proximal femur from digital biplanar radiographs," (2008), 4 pages.
Laporte S., et al., "A biplanar reconstruction method based on 2D and 3D contours: application to the distal femur," (2003), 6 pages.
Japanese Office Action, JP Application No. 2010-546960, dated Mar. 12, 2013, 4 pages.
Japanese Office Action, JP Application No. 2010-546904, dated Mar. 12, 2013, 6 pages.
Japanese Office Action, JP Application No. 2010-546098, dated Mar. 5, 2013, 11 pages.
International Preliminary Report on Patentability, PCT/RU2010/000452, dated Feb. 26, 2013, 9 pages.
Japanese Office Action, JP Application No. 2010-545284, dated Mar. 5, 2013, 6 pages.
European Extended Search Report, Application No. 09707791.1-1654/2240084, PCT/US2009/033258, dated Nov. 21, 2013, 6 pages.

FAST ADJUST EXTERNAL FIXATION CONNECTION ROD

CROSS-REFERENCE TO RELATED APPLICATIONS

This application is a continuation Ser. No. 12/865,057, filed on Jul. 28, 2010, which is a national phase filing under section 371 of PCT/US2009/033975, filed Feb. 12, 2009, which claims the priority of U.S. provisional patent application 61/027,986, filed Feb. 12, 2008, each of which is incorporated herein by reference in its entirety.

TECHNICAL FIELD

The present disclosure relates in general to the field of external fixation, and more specifically, to connection rods having articulatable joints for attachment to the rings or other external supports of the fixation device.

BACKGROUND

Without limiting the scope of the disclosure, this background section is described in connection with external fixation devices and specifically connection rods. Generally, external fixation devices are commonly used in a variety of surgical procedures including limb lengthening, deformity correction, fracture reduction and treatment of non-unions, mal-unions and bone defects. The process involves a rigid framework comprising several rings that are placed externally around the limb and attached to bone segments using wires and half pins inserted into the bone segments and connected to the related section of the external rigid framework. The opposite rings of the rigid framework are interconnected by either threaded or telescopic rods directly or in conjunction with uni-planar or multi-planar hinges, which allow the surgeon to connect opposite rings that are not parallel to each other after manipulation with bone segments either rapidly (acutely) or gradually over a period of time.

For example, in bone fracture reduction or non-union treatment, the wires and half pins are inserted into each bone segment and attached to rings of a rigid framework. The rigid framework is used to acutely reduce a displacement and restore alignment between the bone segments. During the realignment of the bone segments, the orientations of opposite rings often are not parallel. Those opposite rings of the rigid framework are connected together by threaded or telescopic rods with attached uni-planar or multi-planar hinges. This allows the opposite bone segment to be rigidly fixed until complete fracture healing or bone consolidation is completed.

SUMMARY

The present enclosure includes embodiments of a external fixation connection rod that allows for rapid, coarse adjustments of the rod length and is operable to be easily and rigidly attached to non-parallel external fixator rings.

Described in one embodiment is a connecting rod for an external fixation device comprising a telescopic housing having a housing body having an axial bore defined therethrough; a first joint coupled to an end portion of the housing body; and a first rotating member received in the first joint, wherein the first rotating member is operable to rotate relative to the first joint about a first axis. The first rotating member comprises a first connection mechanism operable to releasably couple the first rotating member to a first fixator ring. The connecting rod further includes an adjustment sleeve slidably disposed within the axial bore, the adjustment sleeve and the telescopic housing being releasably coupled by a fastener, and an externally threaded elongated member threadably coupled the adjustment sleeve. The elongated member comprises a threaded rod; a second joint coupled to an end portion of the threaded rod; and a second rotating member received in the second joint, wherein the second rotating member is operable rotate relative to the second joint about a second axis.

The second rotating member comprises a second connection mechanism operable to releasably couple the second rotating member to a second fixator ring. The first and second connection mechanisms are operable to substantially limit the rotational movement of the first and second rotating members, respectively.

In some embodiments the first and second connection mechanisms each comprise a fastener aperture defined in the first and second rotating member, respectively, and each fastener aperture is operable to receive a ring fastener disposed through a bore defined in the first or second ring.

In some embodiments, the first and second joints each comprise a socket, and the first and second rotating members comprise a first and second ball members, respectively, the first and second ball member being disposed in the socket of the first and second joints, respectively. In some exemplary embodiments, the sockets of first and second joints are seated in first and second seating members, respectively, and the seating members each have an inner recessed portion for receiving the socket of first or second joints, and an outer ring contact portion for providing a contact surface with the first or second ring.

In some particular embodiments, the first connection mechanism comprises a first connecting body extending radially from the first ball member, to the outside of the socket of the first joint, and through an aperture defined in the first seating member, and the first connecting body has a threaded portion operable to be inserted through a bore defined in the first ring. The second connection mechanism also comprises a second connecting body extending radially from the second ball member, to the outside of the socket of the second joint, and through an aperture defined in the second seating member, and the second connecting body has a threaded portion operable to be inserted through a bore defined in the second ring. In these embodiments, the threaded portions of the first and second connecting bodies each are operable to receive a mating nut.

The present disclosure also includes embodiments direct to a connecting rod for an external fixation device comprising a telescopic housing having a housing body, in which a first portion of the housing body comprises a first axial bore defined therethrough, and a second portion of the housing body comprises a second axial bore defined therethrough. The first and second axial bores have first and second longitudinal axes, respectively, and the first and second longitudinal axes are parallel and coplanar. The connecting rod further includes first and second sleeves slidably disposed within the first and second axial bores, respectively, and the first sleeve has an adjustment mechanism rotatably disposed on an end portion of the first sleeve. The connect rod further includes an elongated member threadably coupled to the adjustment mechanism such that rotating the adjustment mechanism causes the elongated member to translate along the first axis of the first axial bore. The housing body comprises first and second apertures defined in the walls of the first and second portions of the housing body, respectively, and the first and second apertures are aligned along the first and second axes, respectively. A first fastener is disposed through the first aperture of the housing body and received in a fastener aperture defined in the first sleeve, and a second fastener is disposed through the second aperture of the housing body and received in a fastener aperture defined in the second sleeve, the first and second fasteners being operable to releasably couple the first and second sleeves to the housing body, respectively.

The present disclosure also includes embodiments for a method of maintaining the orientation of first and second fixator rings for immobilizing bone segments. One exemplary embodiment of the disclosed method includes providing a connecting rod comprising a telescopic housing having an axial bore defined therethrough; an adjustment sleeve slidably disposed within the axial bore, the adjustment sleeve and the telescopic housing; and an externally threaded elongated member threadably coupled to the adjustment sleeve. A first joint is coupled to an end portion of the housing, and a first rotating member is received in the first joint. Furthermore, the first rotating member comprises a first connection mechanism operable to releasably couple the first rotating member to the first fixator ring and substantially limit the rotational movement of the first rotating member. A second joint is coupled to an end portion of the housing, and a second rotating member is received in the second joint. Furthermore, the second rotating member comprises a second connection mechanism operable to releasably couple the second rotating member to the second fixator ring and substantially limit the rotational movement of the second rotating member. The disclosed embodiment further includes adjusting the longitudinal position of adjustment sleeve relative to the telescopic housing, and releasably coupling the adjustment sleeve to the telescopic housing using a sleeve fastener. The disclosed embodiment further includes using the first connection mechanism to releasably couple the first rotating member to the first fixator ring and substantially limit the rotational movement of the first rotating member, and using the second connection mechanism to releasably couple the second rotating member to the second fixator ring and substantially limit the rotational movement of the second rotating member.

BRIEF DESCRIPTION OF THE DRAWINGS

For a more complete understanding of the features and advantages of the present disclosure, reference is now made to the detailed description of the disclosure along with the accompanying figures in which.

DETAILED DESCRIPTION

While the making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the disclosure and do not limit the scope of the disclosure.

To facilitate the understanding of this disclosure, a number of terms are defined below. Terms defined herein have meanings as commonly understood by a person of ordinary skill in the areas relevant to the present disclosure. Terms such as "a", "an" and "the" are not intended to refer to only a singular entity, but include the general class of which a specific example may be used for illustration. The terminology herein is used to describe specific embodiments of the disclosure, but their usage does not limit the disclosure, except as outlined in the claims.

The present disclosure includes embodiments directed to an external fixation connection rod with a housing that allows for rapid and gradual adjustment in length and having joint attachments to parallel or non-parallel rings or other external supports. The external fixation connection rod includes a telescopic housing having an axial bore defined therethrough. A first joint is coupled to an end portion of the housing body, and a first rotating member is received in the first joint. The first rotating member is operable to rotate relative to the first joint about a first axis, and comprises a first connection mechanism. The first connection mechanism releasably couples the first rotating member to a first fixator ring.

An adjustment sleeve is slidably disposed within the axial bore of the telescopic housing, and a sleeve fastener is used to secure the adjustment sleeve to the telescopic housing. The adjustment sleeve allows for coarse longitudinal length adjustments with respect to the telescopic housing. In some embodiments, the adjustment sleeve comprises an adjustment mechanism having a rotation element. The rotation element has an internally threaded bore defined therethrough, which allows for threaded connection to a threaded elongated member. The elongated member includes a threaded rod, and the external thread of the threaded rod and the internal thread of the threaded bore mate with each other such that rotating the rotation element causes the threaded elongated member to translate along a longitudinal axis of the connecting rod. Coupled to an end portion of the threaded rod is a second joint and a second rotating member received in the second joint. The second rotating member includes a second connection mechanism operable to releasably couple the second rotating member to a second fixator ring. Additionally, the first and second connection mechanism are operable to substantially limit the rotational movement of the first and second rotating members, respectively.

Figure 1:
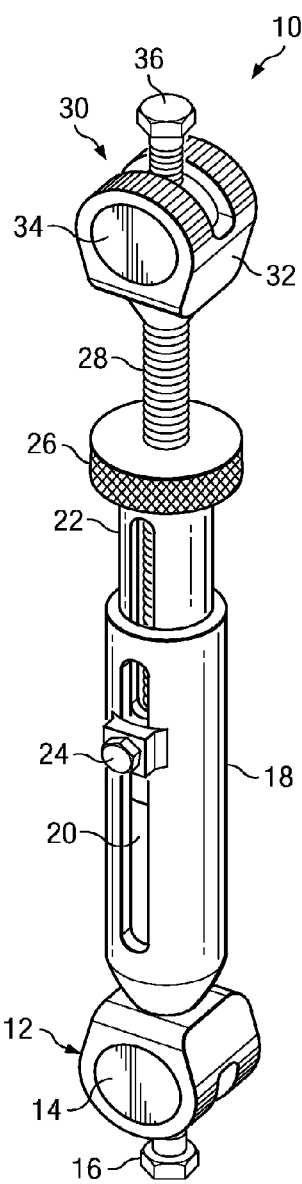
FIG. 1 is a perspective view of one embodiment of an external fixation connection rod of the present disclosure.

FIG. 1 is a perspective view of one embodiment of the external fixation connection rod of the present disclosure. The external fixation connection rod 10 includes a first articulatable joint 12 that houses a first rotating member 14. The first rotating member 14 includes a fastener 16 inserted into a fastener aperture defined (not shown) in the first rotating member 14 to secure the first articulatable joint 12 to an external fixator ring or other fixation device (not shown).

A telescopic housing 18 extends from the first articulatable joint 12 and has an axial bore (not shown) extending longitudinally from the first articulatable joint 12. The first articulatable joint 12 allows angular and rotational alignment of the telescopic housing 18. The telescopic housing 18 includes a telescopic housing adjustment aperture 20 in a wall of the telescopic housing. An adjustment sleeve 22 is positioned in the axial bore (not shown) of the telescopic housing 18. The adjustment sleeve 22 is slidable within the axial bore (not shown) to allow adjustment of the end-to-end length of the connecting rod 10 in a rapid manner. The adjustment sleeve 22 includes a sleeve fastener 24 disposed through the telescopic housing adjustment aperture 20 to secure the adjustment sleeve 22 to the telescopic housing 18.

An adjustment mechanism 26 is positioned at one end of the adjustment sleeve 22 and threadably connected to a threaded elongated member 28. The adjustment mechanism 26 adjusts longitudinally the threaded elongated member 28 to adjust the overall end-to-end length of the connecting rod 10 in a gradual manner. The threaded elongated member 28 includes a second articulatable joint 30 that includes a second articulatable joint housing 32 adapted to fit a second rotating member 34. The second rotating member 34 includes a second fastener 36 that is received in a fastener aperture (not shown) defined in the second rotating member 34 to secure the second articulatable joint 30 to an external fixator ring or other external support (not shown).

Figure 2:
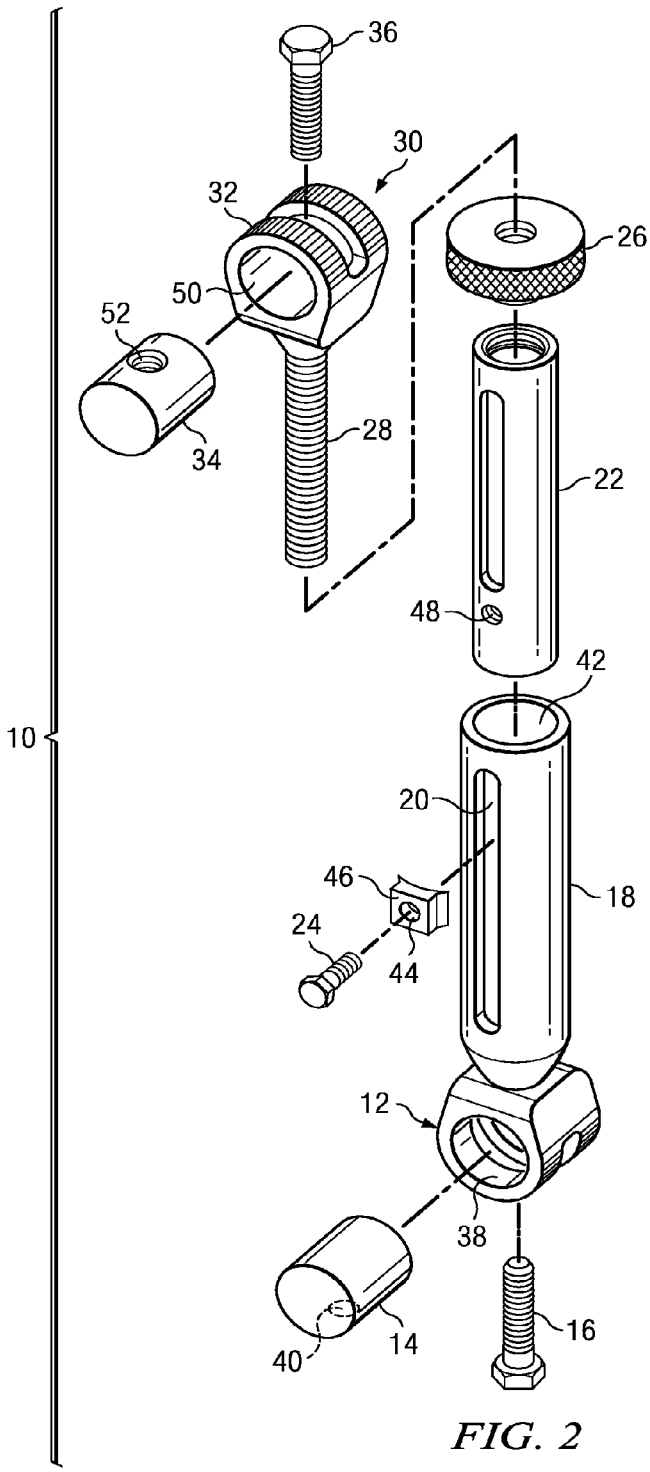
FIG. 2 is an exploded view of the external fixation connection rod of FIG. 1.

FIG. 2 is an exploded view of the embodiment shown in FIG. 1. The external fixation connection rod 10 includes a first articulatable joint 12 that houses a first rotating member 14. The first rotating member 14 passes through a joint aperture 38 that is sized and proportioned to fit the first rotating member 14. A fastener 16 passes through a slot (not shown) in the first articulatable joint 12 and into a fastener aperture 40 defined in the first rotating member 14 to secure the first articulatable joint 12 to an external fixator ring or other external support (not shown). The first articulatable joint 12 allows angular and rotational alignment of the external fixation connection rod 10 relative to the first external fixator ring or other external support.

A telescopic housing 18 extends from the first articulatable joint 12 and has an axial bore (not shown) extending longitudinally from the first articulatable joint 12 to the axial bore aperture 42. The telescopic housing 18 includes a telescopic housing adjustment aperture 20. An adjustment sleeve 22 is slidably disposed within the axial bore (not shown) of the telescopic housing 18. The adjustment sleeve 22 is slidable within the axial bore (not shown) to allow adjustment of the end-to-end length of the external fixation connection rod 10 in a rapid manner. The adjustment sleeve 22 includes a sleeve fastener 24 that is inserted through a central opening 44 defined in a sleeve fastener washer 46 and through the telescopic housing adjustment aperture 20 into a sleeve fastener aperture 48 defined in the adjustment sleeve 22.

An adjustment mechanism 26 is rotatably coupled to an end portion of the adjustment sleeve 22 and threadably connected to a threaded elongated member 28. The adjustment mechanism is operable to rotate but not translate relative to the end portion of the adjustment sleeve 22. The adjustment mechanism 26 adjusts longitudinally the threaded elongated member 28 to adjust the overall end-to-end length of the external fixation connection rod 10 in a gradual manner.

The threaded elongated member 28 includes a second articulatable joint 30. The second articulatable joint 30 includes a second articulatable joint housing 32 adapted to fit a second rotating member 34. The second rotating member 34 passes through a second joint aperture 50 that is sized and proportioned to fit the second rotating member 34. A second fastener 36 disposed through a slot (not shown) in the second articulatable joint 30 and into a second fastener aperture 52 defined in the second rotating member 34 to secure the second articulatable joint 30 to an external fixator ring or other fixation device (not shown). The second articulatable joint 30 allows angular and rotational alignment of the external fixation connection rod 10 relative to the second external fixator ring (not shown) or other external support.

Figures 3, 4:
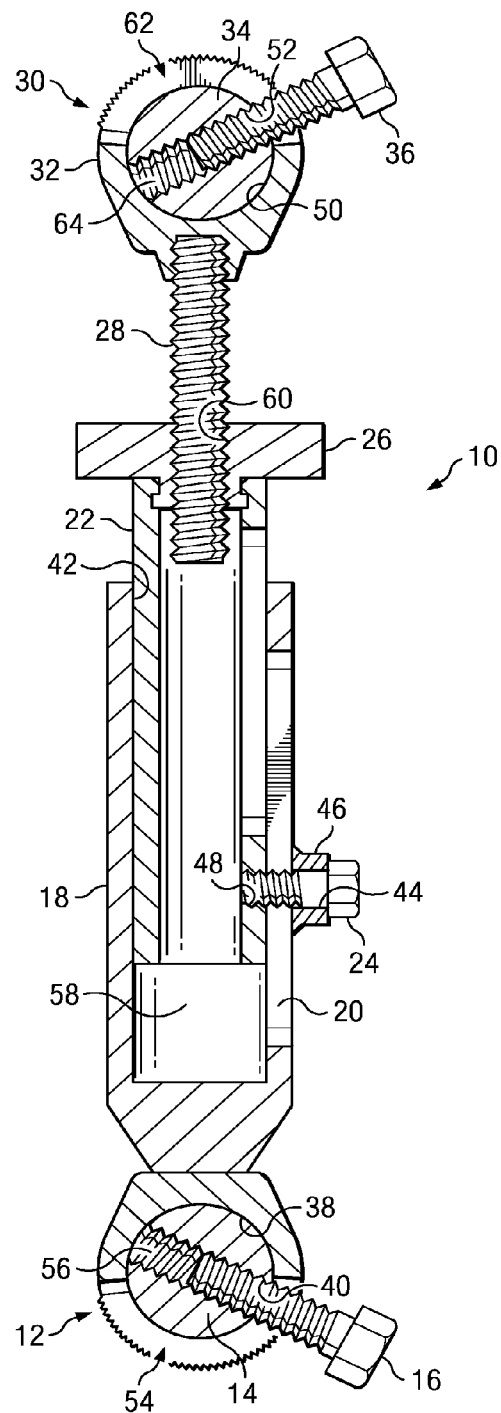
FIG. 3 is a cutaway view of the external fixation connection rod of FIG. 1.
FIG. 4 is a perspective view of a portion of the external fixation connection rod of the present disclosure.

FIG. 3 is a cutaway view of the embodiment shown in FIGS. 1-2. The external fixation connection rod 10 includes a first articulatable joint 12 that houses a first rotating member 14. The first rotating member 14 passes through a joint aperture 38 that is sized and proportioned to fit the first rotating member 14. A fastener 16 is disposed through a slot 54 in the first articulatable joint 12 and fastener aperture 40 into a first threaded bore 56 defined in the first rotating member 14 to secure the first articulatable joint 12 to an external fixator ring or other external support (not shown). The first articulatable joint 12 allows angular and rotational alignment of the external fixation connection rod 10 relative to the first external fixator ring (not shown) or other external support.

A telescopic housing 18 extends from the first articulatable joint 12 and has an axial bore 58 extending longitudinally from the first articulatable joint 12 to the axial bore aperture 42. The telescopic housing 18 includes a telescopic housing adjustment aperture 20. An adjustment sleeve 22 is slidably disposed within the axial bore 58 of the telescopic housing 18. The adjustment sleeve 22 is slidable within the axial bore 58 to allow adjustment of the end-to-end length of the external fixation connection rod 10 in a rapid manner. The adjustment sleeve 22 includes a sleeve fastener 24 that is inserted through a sleeve fastener washer aperture 44 centrally defined in the sleeve fastener washer 46 and through the telescopic housing adjustment aperture (not shown) into a sleeve fastener aperture 48. Alternatively, the sleeve fastener 24 may include a separate sleeve washer 46 as a single unit.

An adjustment mechanism 26 is rotatably disposed at an end portion of the adjustment sleeve 22 and threadably connected to a threaded elongated member 28. In some embodiments, the adjustment mechanism 26 may include a rotation element, the rotation element having an internally threaded bore defined therethrough. The threaded elongated member 28 is disposed through the threaded bore 60 of the rotation element of the adjustment mechanism, and the external thread of the elongated member and the internal thread of the threaded bore mate with each other such that rotating the rotation element of the adjustment mechanism 26 causes the threaded elongated member 28 to translate along a longitudinal axis of the connecting rod.

The adjustment mechanism 26 adjusts longitudinally the threaded elongated member 28 to adjust the overall end-to-end length of the external fixation connection rod 10 in a gradual manner. The threaded elongated member 28 includes a second articulatable joint 30.

The second articulatable joint 30 includes a second articulatable joint housing 32 adapted to fit a second rotating member 34. The second rotating member 34 passes through a second joint aperture 50 that is sized and proportioned to fit the second rotating member 34. A second fastener 36 is inserted through a slot 62 in the second articulatable joint 30 and a second fastener aperture 52 into a second threaded fastener bore 64 to secure the second articulatable joint 30 to an external fixator ring or other external support (not shown). The second articulatable joint 30 allows angular and rotational alignment of the external fixation connection rod 10 relative to the second external fixator ring (not shown) or other external support.

FIG. 4 is a perspective view of a portion of the external fixation connection rod of the present disclosure. The articulatable joint 30 includes an articulatable joint housing 32 adapted to fit a rotating member 34. The rotating member 34 passes through an articulatable joint aperture 50 that is sized and proportioned to fit the rotating member 34. A fastener (not shown) is inserted through a slot 62 in the articulatable joint 30 and a fastener aperture 52 into a threaded fastener bore (not shown) to secure the articulatable joint 30 to an external fixator ring or other external support (not shown). The articulatable joint 30 may be textured 76 to provide increased adhesion or traction to the external fixator ring or other external supports (not shown).

Figures 5, 6:
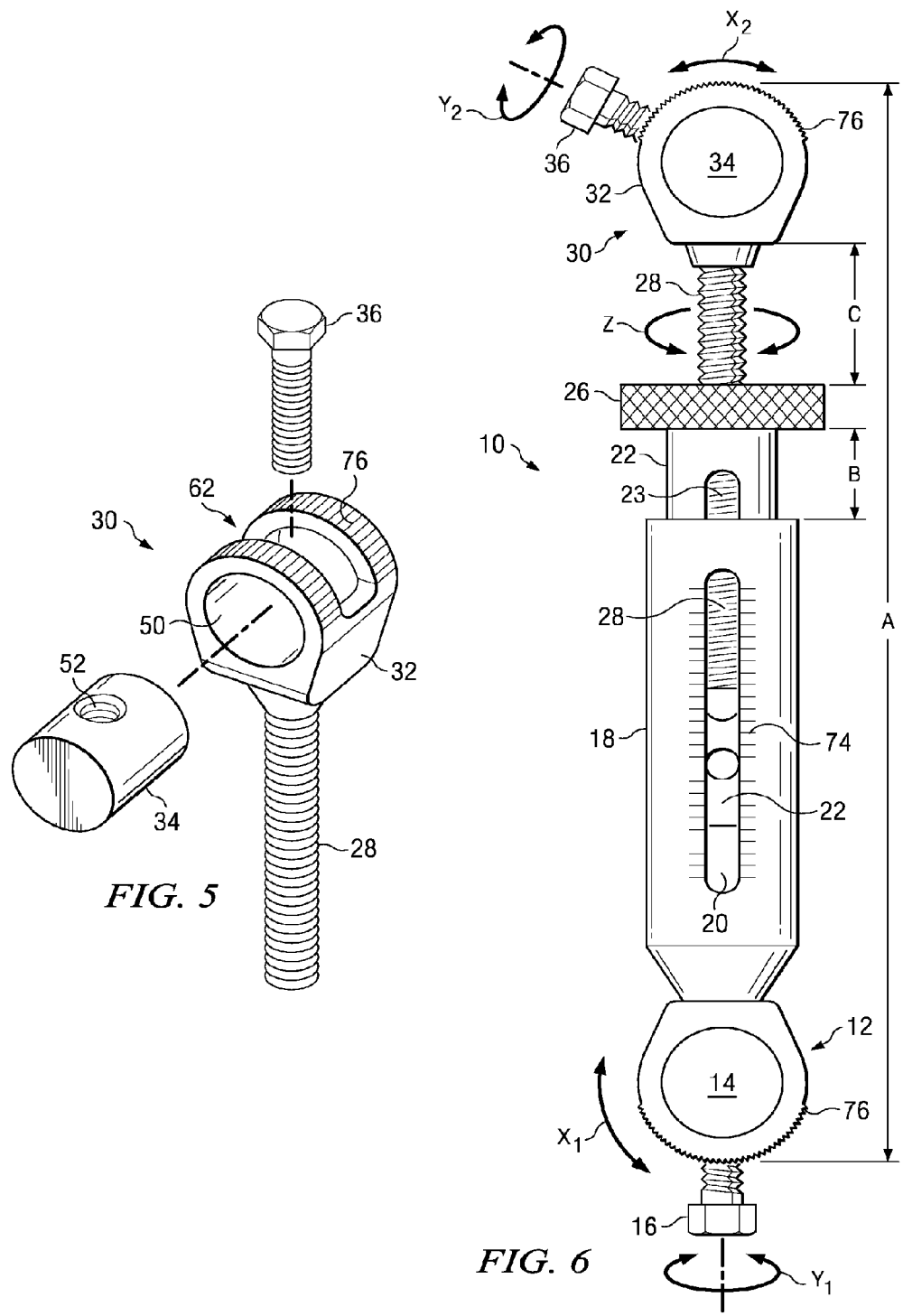
FIG. 5 is an exploded view of the portion of the external fixation connection rod of FIG. 4.
FIG. 6 is a side view of one embodiment of the external fixation connection rod of the present disclosure.

FIG. 5 is an exploded view of a portion of the external fixation connection rod of the present disclosure. The articulatable joint 30 includes an articulatable joint housing 32 adapted to fit a rotating member 34. The rotating member 34 passes through a joint aperture 50 that is sized and proportioned to fit the rotating member 34. A fastener 36 is inserted through a slot 62 in the articulatable joint 30 and a fastener aperture 52 into a threaded fastener bore (not shown) to secure the articulatable joint 30 to an external fixator ring or other external support (not shown). The articulatable joint 30 may be textured 76 to provide increased adhesion or traction to the external fixator ring or other external supports (not shown).

FIG. 6 is a side view of one embodiment of the external fixation connection rod of the present disclosure. The external fixation connection rod 10 includes a first articulatable joint 12 that houses a first rotating member 14. The first rotating member 14 includes a fastener 16 that is inserted through a slot (not shown) in the first articulatable joint 12 to secure the first articulatable joint 12 to an external fixator ring or other external support (not shown). The first articulatable joint 12 may be rotated about the X1 axis of the first rotating member 14 and around the Y1 axis of the fastener 16. This movement allows the first articulatable joint 12 to be secured by the fastener 16 at different angles relative to an external fixator ring or other fixation support (not shown).

A telescopic housing 18 extends from the first articulatable joint 12 and has an axial bore (not shown) extending longitudinally from the first articulatable joint 12. The telescopic housing 18 includes a telescopic housing adjustment aperture 20. An adjustment sleeve 22 is slidably disposed within the axial bore (not shown) of the telescopic housing 18. The adjustment sleeve 22 is slidable within the axial bore (not shown) to allow adjustment of the end-to-end length "A" of the external fixation connection rod 10 in a rapid manner. The movement of the adjustment sleeve 22 in the axial bore (not shown) of the telescopic housing 18 allows the distance "B" to be changed and in turn change the end-to-end length "A" of the external fixation connection rod 10.

The adjustment sleeve 22 includes a sleeve fastener (not shown) disposed through the telescopic housing adjustment aperture 20 to secure the adjustment sleeve 22 to the telescopic housing 18. The telescopic housing adjustment aperture 20 also serves as a window to allow positioning and referencing of the adjustment sleeve 22 and or the threaded elongated member 28 to aid in the adjustment of the end-to-end length "A" of the external fixation connection rod 10 in a rapid manner.

An adjustment mechanism 26 is rotatably disposed at an end portion of the adjustment sleeve 22 and threadably connected to a threaded elongated member 28. The adjustment mechanism 26 may be rotated in direction "Z" to engage the threads of the threaded elongated member 28 and thereby adjust longitudinally the distance "C" and directly affect the end-to-end length "A" of the external fixation connection rod 10 in a gradual manner. The threaded elongated member 28 includes a second articulatable joint 30 that includes a second articulatable joint housing 32 adapted to fit a second rotating member 34. The second rotating member 34 includes a second fastener 36 that is inserted through a slot (not shown) in the second articulatable joint housing 32 to secure the second articulatable joint 30 to an external fixator ring or other external support (not shown).

The second articulatable joint 30 may be rotated about the X2 axis of the second rotating member 34 and around the Y2 axis of the second fastener 36. This movement allows the second articulatable joint 32 to be secured by the fastener 36 at different angles relative to an external fixator ring or other fixation support (not shown). It is not necessary for the first articulatable joint 12 be at the same angle, position or face relative to the second articulatable joint 30. In addition, the first articulatable joint 12, the second articulatable joint 30 or both articulatable joint 30 may be textured 76 to provide increased adhesion or traction to the external fixator ring or other external supports (not shown).

The graduation marks 74 may be calibrated into discrete increments (e.g., one millimeter increments) and may indicate the distance between the first articulatable joint 12 and the second articulatable joint 30 and relate to the end-to-end length "A" of the external fixation connection rod 10.

The graduation marks 74 indicate the lengths of the external fixation connection rod 10 as a relative value, rather than the distance from some predetermined specific length. The graduation marks do not necessarily have to be based on a traditional measuring system, or indicate the effective length of the strut at all. For instance, the graduation marks could indicate the percentage of total rod extension, or daily increments for cases where the translation takes place over an extended period of time. Reference to a neutral position can be useful to set the base members at a predetermined "neutral" position.

Figure 7:
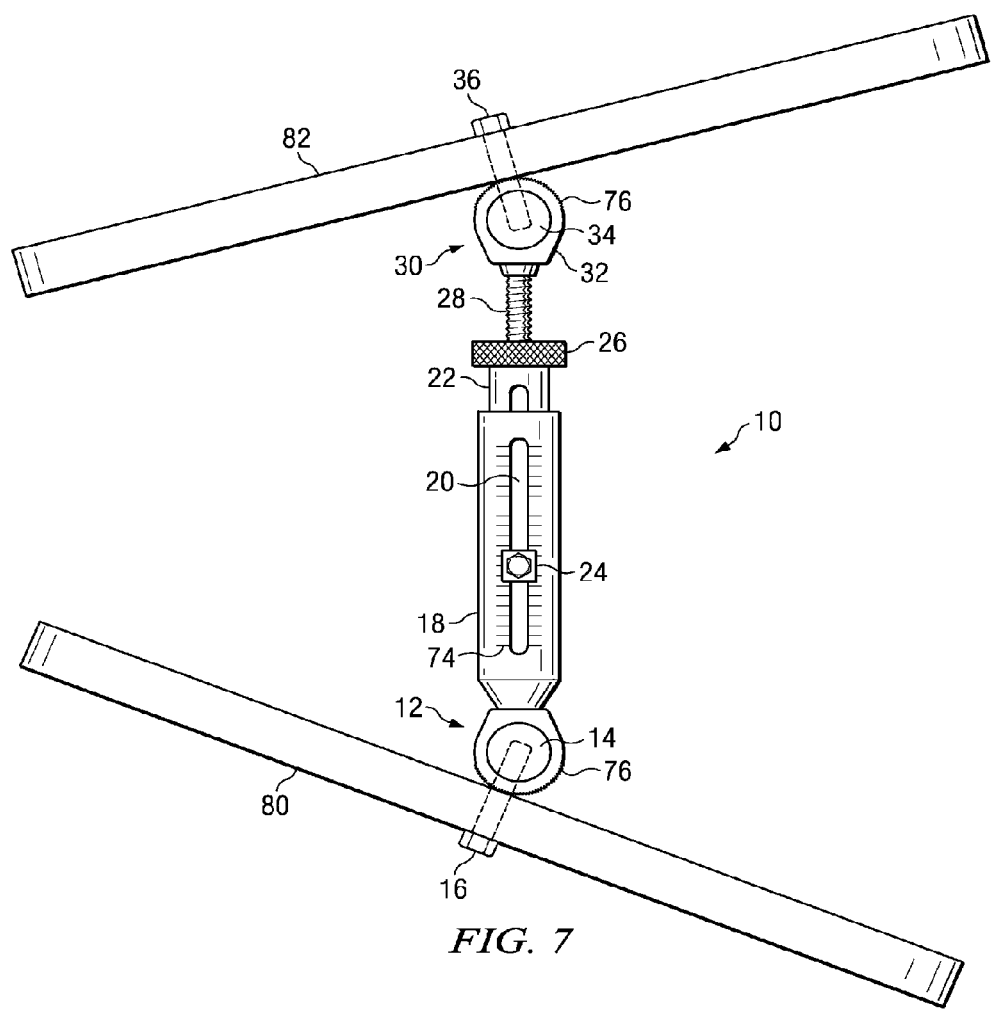
FIG. 7 is a side view of one embodiment of the external fixation connection rod of the present disclosure attached to an external fixation device.

FIG. 7 is a side view of one embodiment of the external fixation connection rod of the present disclosure attached to an external fixation device. An external fixation connection rod 10 is connected between a first external fixator ring 80 and a second external fixator ring 82. FIG. 7 depicts a single external fixation connection rod 10 disposed between the first external fixator ring 80 and the second external fixator ring 82 for simplicity sake. The skilled artisan will readily understand that numerous connecting rods 10 may be attached at various positions about the external fixator rings, that the angle of the external fixation connection rod 10 relative to the first external fixator ring 80 and the second external fixator ring 82 may be varied and the length of the external fixation connection rod 10 may be varied and adjusted.

A first articulatable joint 12 is secured to the external fixator ring 80 or other external support. The external fixation connection rod 10 includes a first articulatable joint 12 that houses a first rotating member 14. The first rotating member 14 includes a fastener 16 that passes through an aperture (not shown) defined in the first external fixator ring 80 and through a slot (not shown) in the first articulatable joint 12 to secure the first articulatable joint 12 to the external fixator ring 80 or other external support. The first rotating member 14 may be rotated to position the fastener 16 at different positions and in turn at different locations in the slot (not shown) of the first articulatable joint 12. This movement allows the first articulatable joint 12 to be secured at different angles relative to an external fixator ring 80 or other external support.

A telescopic housing 18 extends from the first articulatable joint 12 and has an axial bore (not shown) extending longitudinally from the first articulatable joint 12. The telescopic housing 18 includes a telescopic housing adjustment aperture 20. An adjustment sleeve 22 is slidably disposed within the axial bore (not shown) of the telescopic housing 18. The adjustment sleeve 22 is slidable within the bore (not shown) to allow adjustment of the end-to-end length "A" of the connecting rod 10 in a rapid manner.

The adjustment sleeve 22 includes a sleeve fastener 24 positioned through the telescopic housing adjustment aperture 20 to secure the adjustment sleeve 22 to the telescopic housing 18. The telescopic housing adjustment aperture 20 also serves as a window to allow positioning and referencing of the adjustment sleeve 22 and or the threaded elongated member 28 to aid in the adjustment of the end-to-end length of the external fixation connection rod 10. The graduation marks 74 indicate the lengths of the external fixation connection rod 10 as a relative value, rather than the distance from some predetermined specific length. The graduation marks do not necessarily have to be based on a traditional measuring system, or indicate the effective length of the strut at all. For instance, the graduation marks could indicate the percentage of total rod extension, or daily increments for cases where the translation takes place over an extended period of time. Reference to a neutral position can be useful to set the base members at a predetermined "neutral" position.

An adjustment mechanism 26 is rotatably disposed at an end portion of the adjustment sleeve 22 and threadably connected to a threaded elongated member 28. The adjustment mechanism 26 may be rotated to engage the threads of the threaded elongated member 28 and thereby adjust longitudinally the end-to-end length of the connecting rod 10 in a gradual manner. The threaded elongated member 28 includes a second articulatable joint 30 with a second articulatable joint housing 32 adapted to fit a second rotating member 34. The second rotating member 34 includes a second fastener 36 that is inserted through an aperture (not shown) defined in the second external fixator ring 82 and into a slot (not shown) in the second articulatable joint housing 32 to secure the second articulatable joint 30 to an external fixator ring 82 or other external support.

The second articulatable joint 30 may be rotated to position the second fastener 36 at different positions and in turn at different locations in the slot of the second articulatable joint 30. This movement allows the second articulatable joint 30 to be secured at different angles relative to an external fixator ring 82 or other external support. It is not necessary for the first articulatable joint 12 be at the same angle, position or face relative to the second articulatable joint 30. In addition, the first articulatable joint 12, the second articulatable joint 30 or both articulatable joints 30 may be textured 76 to provide increased adhesion or traction to the external fixator ring 80 and 82 or other external supports.

Figure 8:
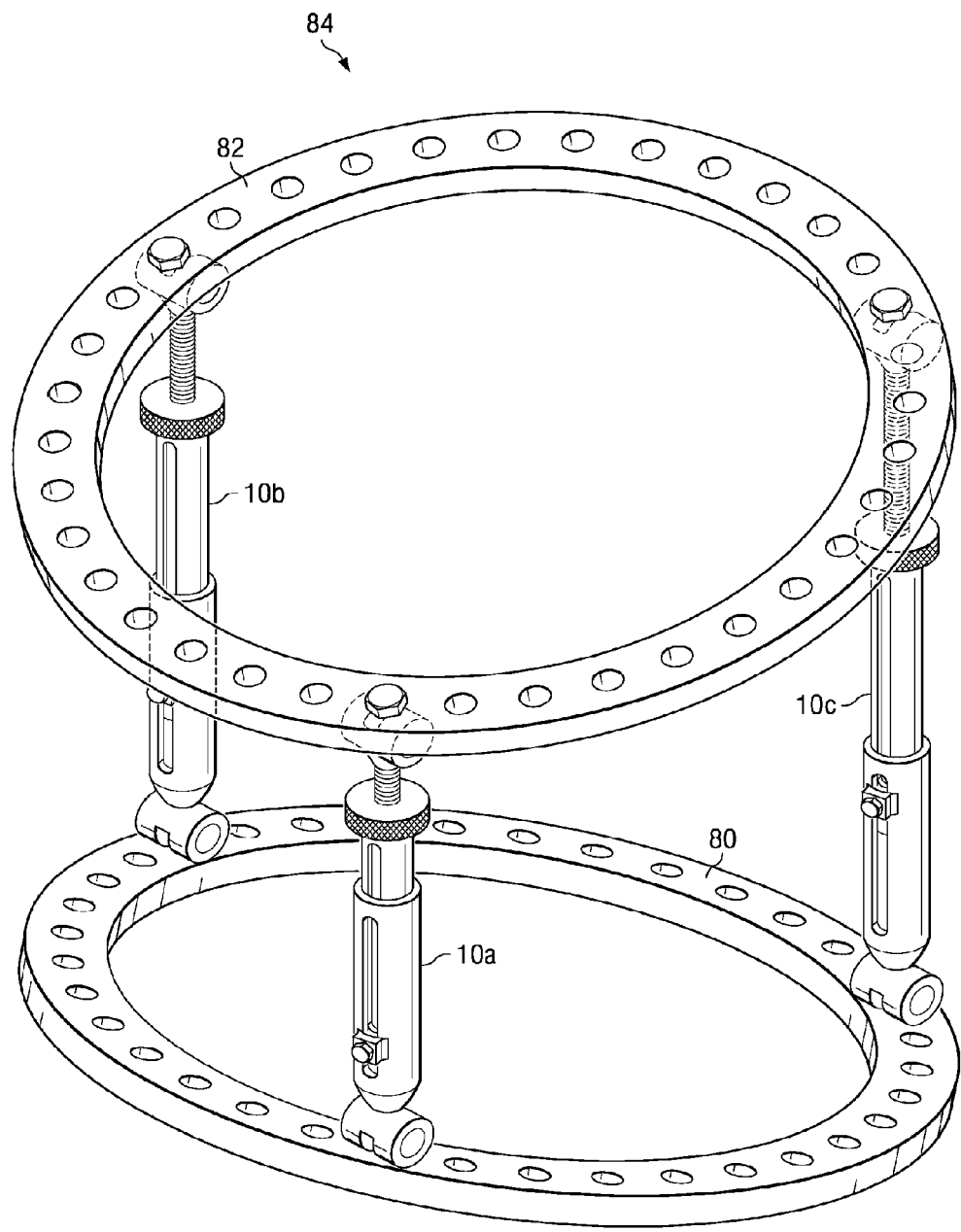
FIG. 8 is a perspective view of one embodiment of the external fixation connection rod of the present disclosure attached to an external fixation device.
Figure 9:
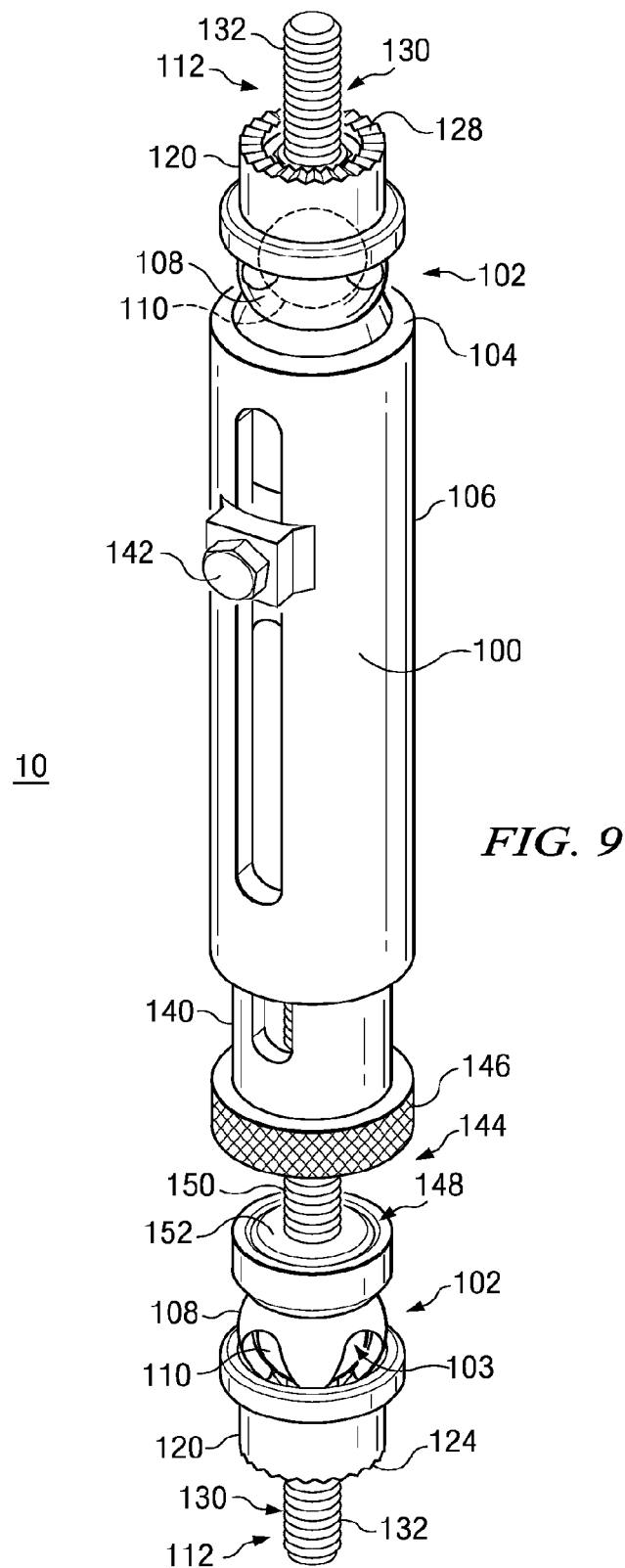
FIG. 9 is a perspective view of another embodiment of an external fixation connection rod of the present disclosure.
Figure 10:
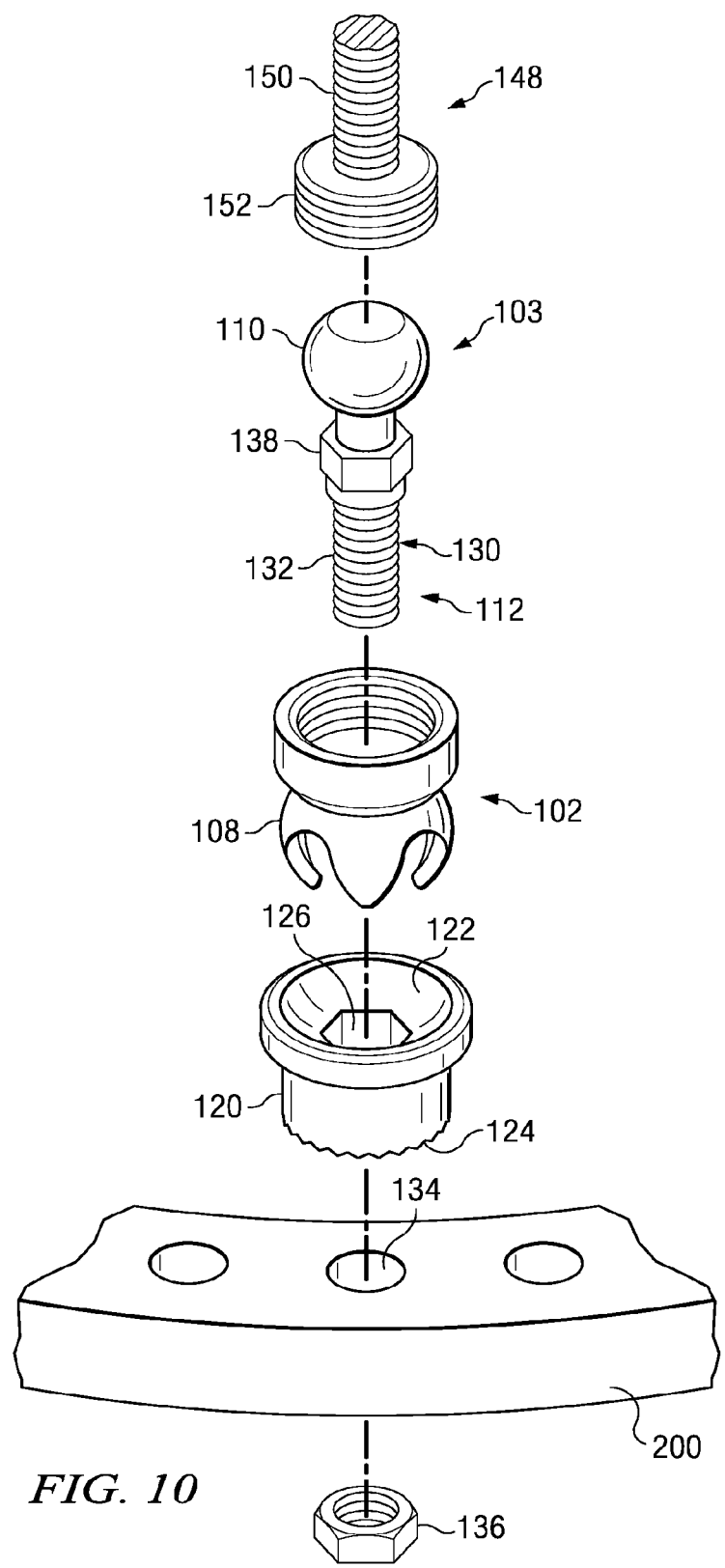
FIG. 10 is an exploded view of a portion of the external fixation connection rod of FIG. 9.
Figure 11:
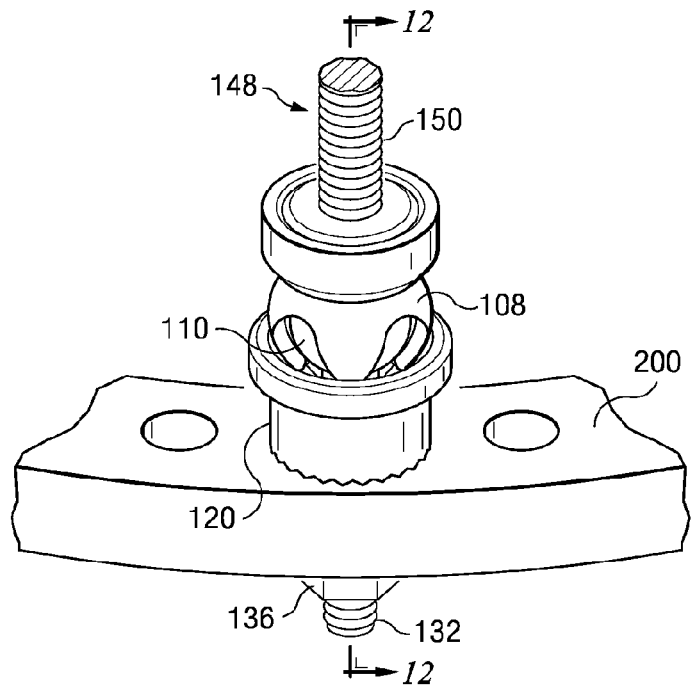
FIG. 11 is an assembled view of the portion of the external fixation connection rod of FIG. 10.
Figure 12:
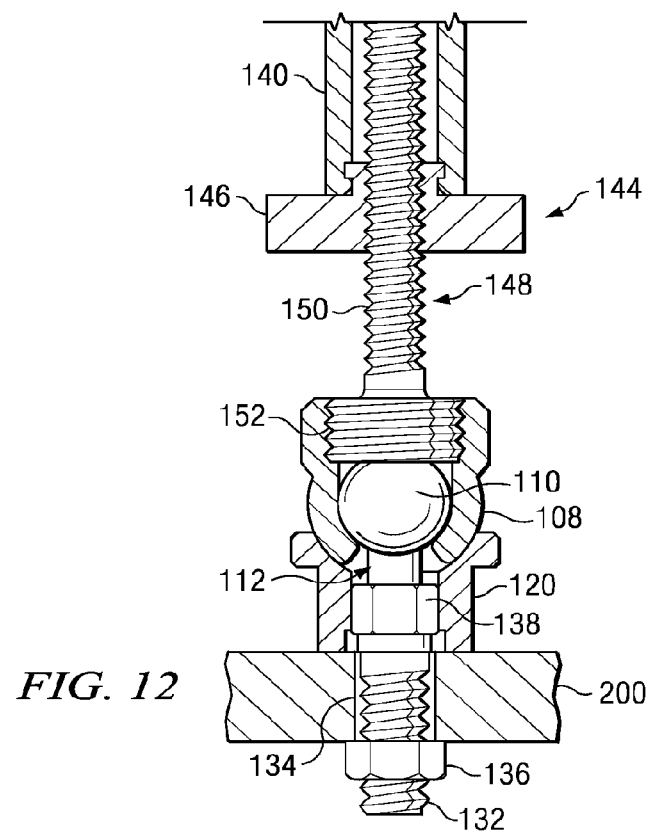
FIG. 12 is a cutway, side view of another portion of the external fixation connection rod of FIG. 9.

FIG. 8 is a perspective view of one embodiment of the external fixation device using the external fixation connection rod of the present disclosure. The external fixation device 84 includes a first external fixator ring 80 and a second external fixator ring 82 connected by one or more external fixation connection rods 10. In this embodiment, there are 3 external fixation connection rods 10a, 10b and 10c. Each of the external fixation connection rods (10a, 10b, and 10c) includes a first articulatable joint that houses a first rotating member. The first rotating member includes a fastener inserted through a slot (not shown) in the first articulatable joint to secure the first articulatable joint to an external fixator ring 80. In other embodiments, the external fixation connection rod 10 may be any connection rods described in this disclosure or constructed in accordance to the principles disclosed herein.

Referring to FIGS. 9-12, an external fixation connection rod 10 includes a telescopic housing 100 having an axial bore (not shown) defined therethrough. A first joint 102 is coupled to an end portion 104 of the housing body 106, and a first rotating member 103 is received in the first joint 102. The first joint 102 includes a socket 108 that may be integrally connected or releasably coupled to the end portion 104 of the housing body 106. The first rotating member 103 includes a ball member 110, which is operable to rotate relative to the socket 108 about a first axis.

In the illustrated embodiment, the external fixation connection rod 10 further includes a seating member 120 having an inner recessed portion 122 for receiving the socket 108 of first joint 102. The seating member 120 further has an outer ring contact portion 124 for providing a contact surface with a first fixator ring 200. In some embodiments, the outer ring contact portion 124 may include grooves 128 defined therein to improve traction with the ring. Although the illustrated embodiment includes seating members 120 to improve the traction with the fixator ring 200, it is to be appreciated that some embodiments may not include a seating member 120.

The first rotating member 103 also includes a first connection mechanism 112 operable to releasably couple the first rotating member 103 to the first fixator ring 200. In the illustrated embodiment, the first connection mechanism 112 includes a first connecting body 130 extending radially from the ball member 110 to the outside of the socket 108 of the first joint 102, and through an aperture defined in the seating member 102. The first connecting body 130 has a threaded portion 132 operable to be inserted through a bore 134 defined in the first ring 200. To lock the ball member 110 and socket 108 to the first ring 200, a nut 136 is disposed over the threaded portion 132, which can be tightened to cause the ball member 110 to exert a pulling force on the socket 108 and seating member 102. In some embodiments, the first connecting body 130 further comprises a flared portion 138, and the aperture 126 defined in the seating member 120 comprises a corresponding interfering portion operable to cooperate with the flared portion 138 of the first connecting body 130 to limit the rotational movement of the ball member 110 relative to the socket 108.

It is to be appreciated that the embodiments discussed herein are merely exemplary, and any of the discussed embodiment can be modified in accordance with the principles disclosed herein. For example, the socket 108 and ball member 110 may be configured to satisfy various design needs. To allow for increased range of motion for the ball member 110, the socket 108 in some embodiments may include a plurality of recessed portions defined in the wall of the socket 108 as illustrated in FIGS. 9-12. Additionally, the recessed portions in the wall of socket 108 allow the ball member 110 and joint 102 to automatically, and without excessive rotation, accommodate the various orientations of the rings 200 as the ball member 110 and socket 108 are being locked to the first ring 200. In the exemplary embodiment illustrated in FIGS. 9-12, the recessed portions are aligned such that they cooperate to form crossed channels.

Also shown in the FIGS. 9-12 is an adjustment sleeve 140 slidably disposed within the axial bore (not shown) of the telescopic housing 100, and a sleeve fastener 142 is used to secure the adjustment sleeve 140 to the telescopic housing 100. The adjustment sleeve 140 allows for coarse longitudinal length adjustments with respect to the telescopic housing 100. In some embodiments, the adjustment sleeve comprises an adjustment mechanism 144 having a rotation element 146, such as a thumb wheel. The rotation element 146 has an internally threaded bore (not shown) defined therethrough, which allows for threaded connection to a threaded elongated member 148. The elongated member includes a threaded rod 150 and the external thread of the threaded rod and the internal thread of the threaded bore mate with each other such that rotating the rotation element 146 causes the threaded elongated member 148 to translate along a longitudinal axis of the connecting rod 10.

Coupled to an end portion 152 of the threaded rod 150 is a second joint 102 and a second rotating member 103 received in the second joint 102. The second rotating member 103 includes a second connection mechanism 112 operable to releasably couple the second rotating member 103 to a second fixator ring 200. In the illustrated embodiment, the configurations of the second joint 102, second rotating member 103, and the second connection mechanism 112 are similar to the configurations of the first joint 102, first rotating member 103, and the first connection mechanism 112 as described above. A seating member 120 can be disposed between the rotating member 103 and the second fixator ring 200 to improve traction as discussed above.

Figure 13:
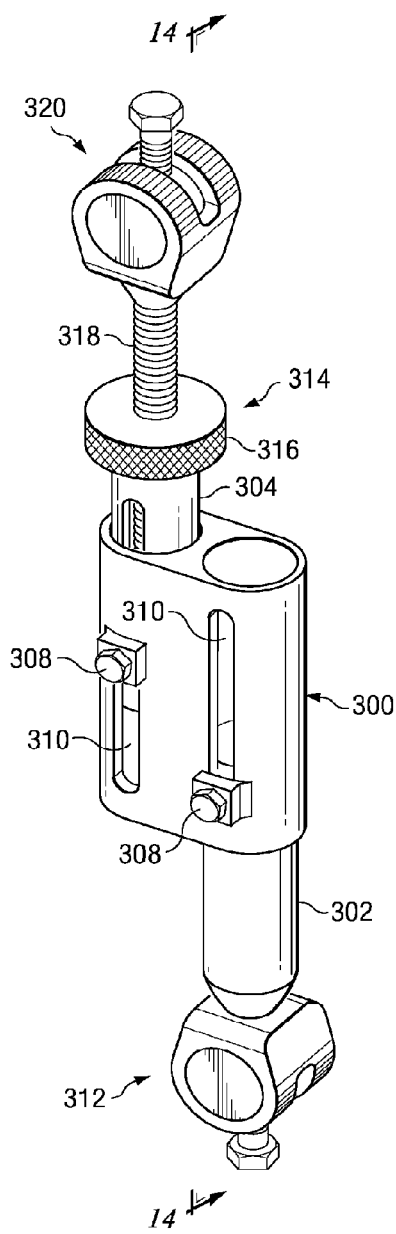
FIG. 13 is a perspective view of yet another embodiment of an external fixation connection rod of the present disclosure.
Figure 14:
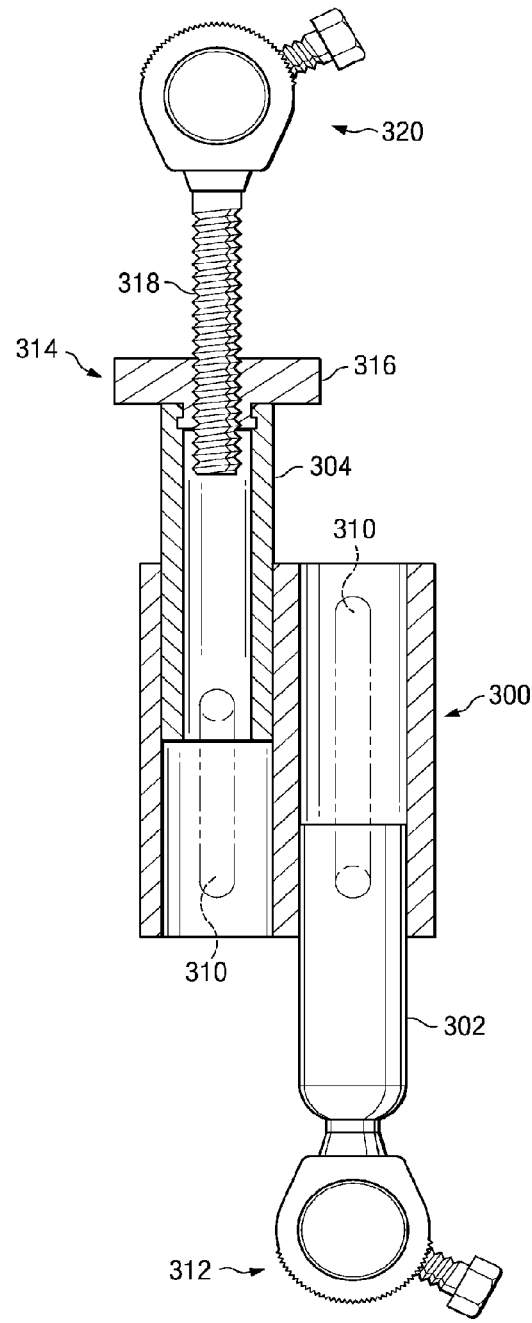
FIG. 14 is a cutway, side view of the external fixation connection rod of FIG. 13.

It is to be appreciated that the embodiments of the present disclosure can be modified in accordance with the principles described herein to satisfy various design constraints. For example, illustrated in FIGS. 13 and 14 is an external fixation connection rod 10 configured to accommodate an external fixation device with a relatively short ring-to-ring length. Specifically, the external fixation connection rod 10 includes a telescopic housing 300 having a housing body, in which a first portion of the housing body 300 comprises a first axial bore defined therethrough, and a second portion of the housing body 300 comprises a second axial bore defined therethrough. The first and second axial bores define first and second longitudinal axes, respectively, and the first and second longitudinal axes are parallel and coplanar. The housing body further comprises first and second apertures 310 defined in the walls of the first and second portions of the housing body 300, respectively. The first and second apertures 300 are aligned along the first and second axes, respectively. Sleeves 302 and 304 are slidably disposed in the first and second axial bores, respectively, and each include a fastener aperture (not shown) defined therein. Fasteners 308 are inserted through the housing apertures 310 and received in the fastener apertures of the first and second sleeves 302 and 304 to lock the sleeves in a desired longitudinal position. As such, the longitudinal movement of the sleeves 302 and 304 in the axial bores allows for coarse length adjustments.

To provide a means for gradual length adjustment, the sleeve 304 further includes an adjustment mechanism 314 having a rotation element 316. The rotation element 316 is rotatably disposed on an end portion of the sleeve 304, and has an internally threaded bore defined therethrough. A threaded elongated member 318 is disposed through the threaded bore of the rotation element 316 of the adjustment mechanism 314. The external thread of the elongated member and the internal thread of the threaded bore engage each other such that rotating the rotation element 316 causes the threaded elongated member 318 to translate along a longitudinal axis of the connecting rod. A joint 320 is disposed on an end portion of the threaded elongated member 318 for connection with an external ring or support device. The joint 312 may be any suitable joints or connectors described in the present application or known in the art. The sleeve 302 also includes a joint 312 at an end portion for connection with an external ring or support device. The joint 312 may be any suitable joints or connectors described in the present application or known in the art.

In some embodiments, the sleeve 302 can also include a second adjustment mechanism rotatably disposed on an end portion of the second sleeve. The second adjustment mechanism is threadably coupled to a second elongated member, and rotating the second adjustment mechanism causes the second elongated member to translate along the second axis of the second axial bore.

The present disclosure also includes embodiments for maintaining the orientation of first and second fixator rings for immobilizing bone segments. One exemplary embodiment includes providing a connecting rod comprising a telescopic housing having an axial bore defined therethrough; an adjustment sleeve slidably disposed within the axial bore, the adjustment sleeve and the telescopic housing; and an externally threaded elongated member threadably coupled the adjustment sleeve. A first joint is coupled to an end portion of the housing, and a first rotating member is received in the first joint. Furthermore, the first rotating member comprises a first connection mechanism operable to releasably couple the first rotating member to the first fixator ring and substantially limit the rotational movement of the first rotating member. A second joint is coupled to an end portion of the housing, and a second rotating member is received in the second joint. Furthermore, the second rotating member comprises a second connection mechanism operable to releasably couple the second rotating member to the second fixator ring and substantially limit the rotational movement of the second rotating member. The disclosed embodiment further includes adjusting the longitudinal position of adjustment sleeve relative to the telescopic housing, and releasably coupling the adjustment sleeve to the telescopic housing using a sleeve fastener. The disclosed embodiment further includes using the first connection mechanism to releasably couple the first rotating member to the first fixator ring and substantially limit the rotational movement of the first rotating member, and using the second connection mechanism to releasably couple the second rotating member to the second fixator ring and substantially limit the rotational movement of the second rotating member.

The methods of the present disclosure may be performed with a subject, e.g., a human or another vertebrate animal. One or more bones (of the subject) to be fixed may be selected. Any suitable bone(s) may be selected, such as a long bone(s) and/or at least a pair of bones connected via an anatomical joint. Exemplary bones include leg bones (femur, tibia, and fibula), arm bones (humerus, radius, and ulna), foot bones (calcaneus, talus, metatarsals, and phalanges), wrist/hand bones (carpals, metacarpals, and phalanges), etc. In exemplary embodiments, one or more bones including at least one long bone may be selected.

An external fixation device may be constructed along and at least partially around the selected bone(s). The external fixation device may include a plurality of rings fixed in position relative to one another by numerous connecting rods secured to the rings.

The external fixation device may be connected to the selected bone(s). Connection may be performed at any suitable time, such as before, during, and/or after construction of the external fixation device. For example, the external fixation device may be assembled and then connected to bone, or individual external fixation device members or external fixation device sub-assemblies may be connected to the bone before the external fixation device is fully assembled. Connection of the external fixation device to bone may include placing connectors, such as wires, pins, screw, and/or rods, among others, through the skin and into, through, and/or around the selected bone.

The external fixation device may be reconfigured while it is connected to the one or more selected bones. Reconfiguration may include adjusting the length, angle, position, and/or connection site of one or more external fixation device components, particularly connecting rod. In some embodiments, reconfiguration may involve lengthening and/or shortening one or more (or all) connecting rods of the external fixation device. In some embodiments, reconfiguration may involve replacing one or more connecting rods with a different connecting rod(s). The different connecting rod may be of different size, pivotability, adjustability, shape, and/or the like.

The external fixation device may be braced to facilitate reconfiguration. Bracing the external fixation device may stiffen and/or stabilize the external fixation device such that reconfiguration produces fewer undesired changes to the external fixation device structure as the external fixation device is weakened and altered during reconfiguration. Bracing may be performed by a pair of connecting rods of the external fixation device. In some examples, the brace may be configured to be clipped onto the external fixation device members before the brace is fully secured to the external fixation device members. For example, the brace may include one or more external fixation device engagement elements that are biased to opposingly engage one or more respective external fixation device members. In any case, each engagement element may be secured in place on the external fixation device member by operating a user control, manually or with a tool. Furthermore, the relative spacing and angular disposition of the engagement elements may be fixed by operating a user control, either the same user control(s) for securing the engagement element to a frame member or a distinct user control.

In some examples, the brace may include one or more movable joints, and the brace may be installed in engagement with the external fixation device members with one or more of the joints in a movable configuration. The movable joints then may be adjusted to a locked (fixed) configuration. Alternatively, or in addition, the brace may include a plurality of movable joints and one or more of the movable joints may be locked before or during brace placement onto the frame, and one or more other of the movable joints may be locked after brace placement onto the external fixation device.

The brace may be removed after frame reconfiguration. Accordingly, the brace may be installed with the frame (and connecting rod) fixing bone and removed with the frame reconfigured and still fixing bone. The brace thus may be present on the external fixation device for only a fraction of the time that the external fixation device is fixing bone.

It is contemplated that any embodiment discussed in this specification can be implemented with respect to any method, kit, reagent, or composition of the disclosure, and vice versa. Furthermore, compositions of the disclosure can be used to achieve methods of the disclosure.

It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A connecting rod for an external fixation device, the connecting rod defining a longitudinal axis and comprising:
   a telescopic housing comprising:
      a housing body having an axial bore defined therethrough;
      a first joint coupled to an end portion of the housing body; and a first rotating member received in the first joint, wherein the first rotating member is operable to rotate relative to the first joint about a first axis orthogonal to the longitudinal axis of the connecting rod, and the first rotating member comprises a first connection mechanism operable to releasably couple the first rotating member to a first ring;

an adjustment sleeve slidably disposed within the axial bore, the adjustment sleeve and the telescopic housing being releasably coupled by a fastener; and an elongated member coupled to the adjustment sleeve, the elongated member comprising:
  a rod;
  a second joint coupled to an end portion of the rod;
  a second rotating member received in the second joint, wherein the second rotating member is operable to rotate relative to the second joint about a second axis orthogonal to the longitudinal axis of the connecting rod, and the second rotating member comprises a second connection mechanism operable to releasably couple the second rotating member to a second ring;

wherein, the first and second connection mechanisms are operable to substantially limit the rotational movement of the first and second rotating members, respectively; and wherein at least one of the first and second joints comprises a slot, the respective connection mechanism is operable to releasably couple the respective rotating member to the respective fixator ring using a ring fastener passing through the slot and coupled to the respective rotating member, and the cooperation of the slot and the ring fastener limit the rotation of the respective rotating member.

2. The connecting rod of claim 1, wherein the first and second connection mechanisms each comprise a fastener aperture defined in the first and second rotating members, respectively, and further wherein each fastener aperture is operable to receive a ring fastener disposed through a bore defined in the first or second ring.

3. The connecting rod of claim 2, wherein the first joint comprises a textured surface operable to provide frictional contact with a surface of the first ring.

4. The connecting rod of claim 3, wherein the textured surface comprises parallel grooves defined therein.

5. The connecting rod of claim 2, wherein the second joint comprises a textured surface operable to provide frictional contact with a surface of the second ring.

6. The connecting rod of claim 5, wherein the textured surface comprises parallel grooves defined therein.

7. The connecting rod of claim 1, wherein the telescopic housing comprises an aperture defined in a wall of the housing, the aperture extending longitudinally along the housing, and the adjustment sleeve comprises a threaded radial bore, and further wherein the fastener comprises a screw inserted through the aperture of the telescopic housing and received in the threaded radial bore.

8. The connecting rod of claim 7, further comprising a washer having a central opening defined therein, the washer being disposed on an outer surface of the telescopic housing, and further wherein the screw is inserted through the central opening of the washer, through the aperture of the telescopic housing, and received in the threaded radial bore.

9. The connecting rod of claim 1, wherein the adjustment sleeve comprises an aperture defined in a wall of the adjustment sleeve, the aperture extending longitudinally along the adjustment sleeve.

10. The connecting rod of claim 1, wherein the elongated member is an externally threaded elongated member, the adjustment sleeve comprises an adjustment mechanism having a rotation element, the rotation element having an internally threaded bore defined therethrough, wherein the threaded elongated member is disposed through the threaded bore of the rotation element of the adjustment mechanism, the external thread of the elongated member and the internal thread of the threaded bore mating with each other such that rotating the rotation element causes the threaded elongated member to translate along the longitudinal axis of the connecting rod.

11. The connecting rod of claim 10, wherein the adjustment mechanism is rotatably coupled to an end portion of the adjustment sleeve, the adjustment mechanism being operable to rotate but not translate relative to the end portion of the adjustment sleeve.

12. A method of maintaining the orientation of first and second rings for immobilizing bone segments, comprising:
  providing a connecting rod having a longitudinal axis and comprising:
    a telescopic housing comprising an axial bore defined therethrough;
    an adjustment sleeve slidably disposed within the axial bore, the adjustment sleeve and the telescoping housing being operable to be releasably coupled by a sleeve fastener; and
    an elongated member coupled to the adjustment sleeve;
    wherein a first joint is coupled to an end portion of the housing, and a first rotating member is received in the first joint, and further wherein the first rotating member comprises a first connection mechanism operable to releasably couple the first rotating member to the first ring and substantially limit the rotational movement of the first rotating member; and
    wherein a second joint is coupled to an end portion of the elongated member, and a second rotating member is received in the second joint, and further wherein the second rotating member comprises a second connection mechanism operable to releasably couple the second rotating member to the second ring and substantially limit the rotational movement of the second rotating member;
  adjusting the longitudinal position of the adjustment sleeve relative to the telescopic housing, thereby rotating the first and second rotating members about first and second axes, respectively, wherein the first and second axes are both orthogonal to the longitudinal axis of the connecting rod;
  releasably coupling the adjustment sleeve to the telescopic housing using the sleeve fastener;
  using the first connection mechanism to releasably couple the first rotating member to the first ring and substantially limit the rotational movement of the first rotating member; and
  using the second connection mechanism to releasably couple the second rotating member to the second ring and substantially limit the rotational movement of the second rotating member;
  wherein at least one of the first and second joints comprises a slot, the respective connection mechanism is operable to releasably couple the respective rotating member to the respective fixator ring using a ring fastener passing through the slot and coupled to the respective rotating member, and the cooperation of the slot and the ring fastener limit the rotation of the respective rotating member.

13. The method of claim 12, wherein the first and second connection mechanisms each comprise a fastener aperture defined in the first and second rotating members, respectively, and wherein the method further comprises: disposing ring fasteners through bores defined in the first and second ring and into the fastener apertures of the first and second rotating members, whereby the rotational movements of the first and second rotating members are substantially limited.

14. The method of claim 12, wherein the telescopic housing comprises an aperture defined in a wall of the housing, the aperture extending longitudinally along the housing, and wherein the method further comprises monitoring acute translation of the adjustment sleeve relative to the telescopic housing.

15. The method of claim 12, wherein the adjustment sleeve comprises an aperture defined in a wall of the adjustment sleeve, the aperture extending longitudinally along the adjustment sleeve, and wherein the method further comprises monitoring gradual translation of the elongated member relative to the adjustment sleeve.

16. A connecting rod for an external fixation device comprising:
- a telescopic housing having a housing body, wherein a first portion of the housing body comprises a first axial bore defined therethrough, and a second portion of the housing body comprises a second axial bore defined therethrough, the first and second axial bores having first and second longitudinal axes, respectively, and further wherein the first and second longitudinal axes are parallel and coplanar;
- first and second sleeves slidably disposed within the first and second axial bores, respectively, the first sleeve having an adjustment mechanism rotatably disposed on an end portion of the first sleeve; and
- an elongated member coupled to the adjustment mechanism;
- wherein the housing body comprises first and second apertures defined in walls of the first and second portions of the housing body, respectively, the first and second apertures being aligned along the first and second axes, respectively;
- wherein a first fastener is disposed through the first aperture of the housing body and received in a fastener aperture defined in the first sleeve, and a second fastener is disposed through the second aperture of the housing body and received in a fastener aperture defined in the second sleeve, the first and second fasteners being operable to releasably couple the first and second sleeves to the housing body, respectively; and
- wherein a joint coupled either to an end portion of the elongated member or an end portion of the second sleeve comprises a slot, a connection mechanism and a rotating member, the connection mechanism is operable to releasably couple the rotating member to a fixator ring using a fastener passing through the slot and coupled to the rotating member, and the cooperation of the slot and the fastener limit the rotation of the rotating member.

17. The connecting rod of claim 16, wherein the joint is coupled to an end portion of the elongated member.

18. The connecting rod of claim 16, wherein the joint is coupled to an end portion of the second sleeve.

19. The connecting rod of claim 16, wherein the second sleeve has a second adjustment mechanism rotatably disposed on an end portion of the second sleeve, the second adjustment mechanism being coupled to a second elongated member.

20. The connecting rod of claim 19, further comprising a second joint coupled to an end portion of the second elongated member.

* * * * *